US008889867B2

(12) United States Patent
Clark et al.

(10) Patent No.: US 8,889,867 B2
(45) Date of Patent: *Nov. 18, 2014

(54) SOLID FORMS AND PROCESS FOR PREPARING

(71) Applicant: Corcept Therapeutics, Inc., Menlo Park, CA (US)

(72) Inventors: Robin Clark, Lawai, HI (US); Doug Fry, Euclid, OH (US)

(73) Assignee: Corcept Therapeutics, Inc., Menlo Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/889,130

(22) Filed: May 7, 2013

(65) Prior Publication Data

US 2013/0245266 A1    Sep. 19, 2013

Related U.S. Application Data

(63) Continuation of application No. 12/777,340, filed on May 11, 2010, now Pat. No. 8,461,172.

(60) Provisional application No. 61/177,483, filed on May 12, 2009.

(51) Int. Cl.
*C07D 471/04* (2006.01)

(52) U.S. Cl.
CPC .................................. *C07D 471/04* (2013.01)
USPC ............................................. 546/83; 514/293

(58) Field of Classification Search
CPC ...................................................... C07D 471/04
USPC .............................................. 546/83; 514/293
See application file for complete search history.

(56) References Cited

U.S. PATENT DOCUMENTS

| 7,928,237 | B2 | 4/2011 | Clark et al. |
| 2007/0281928 | A1 | 12/2007 | Clark et al. |
| 2008/0070950 | A1 | 3/2008 | Benjamin et al. |

OTHER PUBLICATIONS

Wikepedia, defination of Amorphous solid—Jan. 16, 2014.*
CNRS, Amorphous Materials, how some solids flow like liquids.—Jul. 2008.*
Declaration by Robin Clark Feb. 2013.*
International Search Report and Written Opinion, dated Jul. 9, 2010, issued in related International Patent Application No. PCT/US2010/034382, filed May 11, 2010.
Clark et al., "1H-Pyrazolo[3,4-g]hexahydro-isoquinolines as selective glucocorticoid receptor antagonists with high functional activity," 2008, Bioorganic & Medical Chemistry Letters, 18, pp. 1312-1317.
Wayne Genck. 2004, Chemical Processing .com.

* cited by examiner

*Primary Examiner* — Rita Desai
(74) *Attorney, Agent, or Firm* — Kilpatrick Townsend and Stockton LLP

(57) ABSTRACT

The present invention provides amorphous solid forms of the compound of Formula I, as well as methods for preparing the compound of Formula I by precipitation.

14 Claims, 3 Drawing Sheets

SOLID FORMS AND PROCESS FOR PREPARING

CROSS-REFERENCE TO RELATED APPLICATIONS

This application is a continuation of U.S. application Ser. No. 12/777,340, filed May 11, 2010, which claims priority to U.S. Provisional Application No. 61/177,483, filed May 13, 2009, incorporated herein in their entirety.

BACKGROUND OF THE INVENTION (R)-4a-ethoxymethyl-1-(4-fluoro-phenyl)-6-(4-trifluoromethyl-benzenesulfonyl)-4,4a,5,6,7,8-hexahydro-1H,1,2,6-triaza-cyclopenta[b]naphthalene (herein Compound 1) was previously published in Clark et al., *Bioorganic and Medicinal Chemistry Letters* 2008, 18, 1312-1317, and has the following structure:

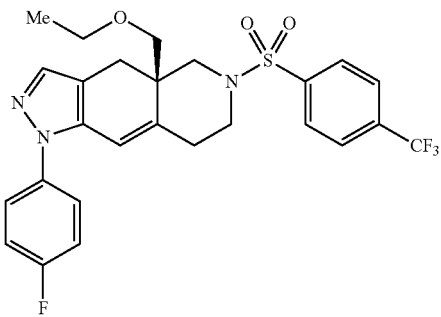 [SMILES: CCOC[C@]12Cc3cnn(-c4ccc(F)cc4)c3C=C1CCN(S(=O)(=O)c1ccc(C(F)(F)F)cc1)C2]

Compound 1 is a member of a class of compounds useful for the modulation of cortisol by glucocorticoid receptor (GR) antagonists. One such known GR antagonist, mifepristone, has been found to be an effective anti-glucocorticoid agent in humans (Bertagna (1984) *J. Clin. Endocrinol. Metab.* 59:25). Mifepristone binds to the GR with high affinity, with a dissociation constant ($K_d$) of $10^{-9}$ M (Cadepond (1997) *Annu. Rev. Med.* 48:129).

Increased levels of cortisol have been found in patients with some forms of psychiatric illnesses (Krishnan (1992) *Prog. Neuro-Psychophannacol. & Biol. Psychiat.* 16:913-920). For example, some depressed individuals can be responsive to treatments which block the effect of cortisol, as by administering GR antagonists (Van Look (1995) *Human Reproduction Update* 1:19-34). In one study, a patient with depression secondary to Cushing's Syndrome (hyperadrenocorticism) was responsive to a high dose, up to 1400 mg per day, of GR antagonist mifepristone (Nieman (1985) *J. Clin Endocrinol. Metab.* 61:536). Another study which used mifepristone to treat Cushing's syndrome found that it improved the patients' conditions, including their psychiatric status (Chrousos, pp 273-284, In: Baulieu, ed. *The Antiprogestin Steroid RU 486 and Human Fertility Control. Plenum Press*, New York (1989), Sartor (1996) *Clin. Obstetrics and Gynecol.* 39:506-510).

Psychosis has also been associated with Cushing's syndrome (Gerson (1985) *Can. J. Psychiatry* 30:223-224; Saad (1984) *Am. J. Med.* 76:759-766). Mifepristone has been used to treat acute psychiatric disturbances secondary to Cushing's syndrome. One study showed that a relatively high dose of mifepristone (400 to 800 mg per day) was useful in rapidly reversing acute psychosis in patients with severe Cushing Syndrome due to adrenal cancers and ectopic secretion of ACTH from lung cancer (Van der Lely (1991) *Ann. Intern. Med.* 114:143; Van der Lely (1993) *Pharmacy World & Science* 15:89-90; Sartor (1996) supra).

Treatment of psychotic major depression and other conditions and diseases using compound 1 would be made easier if compound 1 could be administered in a solid form. Solid forms offer several advantages over oil and gum forms of compounds, such as ease of handling, solubility, formulation with pharmaceutical excipients into solid dosage forms, among others. Previous preparations of compound 1, and derivatives thereof, however, have been unable to produce solid forms of compound 1. See *Bioorganic and Medicinal Chemistry Letters* 2008, 18, 1312-1317, and U.S. patent application Ser. No. 10/591,884 (filed May 7, 2007 and published Dec. 6, 2007 as U.S. Published Application No. 2007/0281928).

What is needed is a solid form of compound 1, and a method for preparing the solid form. Surprisingly, the present invention meets this and other needs.

BRIEF SUMMARY OF THE INVENTION

In one embodiment, the present invention provides an amorphous solid form of a compound of Formula I:

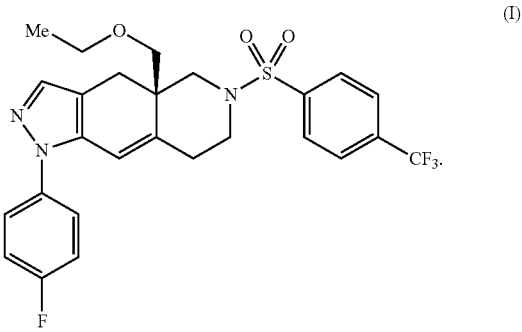 [SMILES: CCOC[C@]12Cc3cnn(-c4ccc(F)cc4)c3C=C1CCN(S(=O)(=O)c1ccc(C(F)(F)F)cc1)C2]

In another embodiment, the present invention provides a method of preparing an amorphous solid form of a compound of Formula I. In one step, the method involves dissolving the compound of Formula I in a solvent of acetone, methanol, ethanol, 2-propanol or 2-methoxyethanol, to prepare a first solution. In another step, the method involves contacting the first solution with water, thereby precipitating the compound of Formula I.

DETAILED DESCRIPTION OF THE INVENTION

Figure 1:
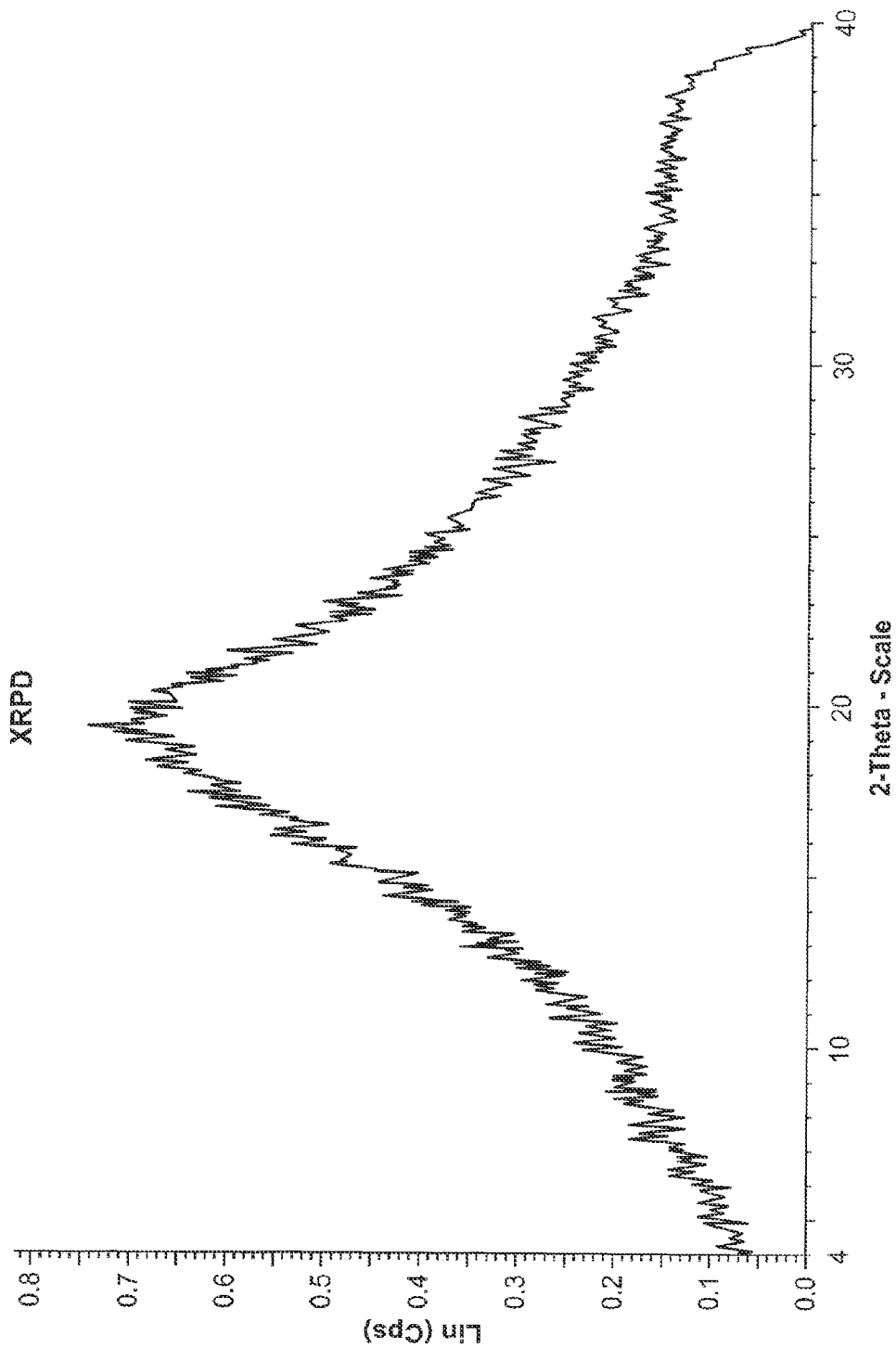
FIG. 1 shows the X-ray diffraction pattern of the compound of Formula I, and demonstrates that the compound of Formula I is amorphous.

The present invention provides an amorphous solid form of the compound of Formula I, and methods for preparing the amorphous solid form. The compound of Formula I is known in the prior art, but not in a solid form. Solid forms of compounds are common and can be prepared by precipitation or crystallization methods using single or binary solvent systems known to one of skill in the art. A variety of solvent systems can be used to prepare the amorphous or crystalline forms of a compound. In some cases, such as with the compound of Formula I, a compound does not readily form an amorphous or a crystalline form, and can require extensive experimentation to identify a solvent system and conditions for preparing the amorphous or crystalline form.

Because the compound of Formula I does not readily form an amorphous or crystalline form, extensive experimentation with a variety of methods and solvent systems was undertaken to prepare a solid form of the compound of Formula I. Some of the methods tested used a single solvent system of dichloromethane, chlorobenzene, toluene, anisole, heptane, 1,4-dioxane, tert-butylmethyl ether, butyl acetate, isopropyl acetate, ethyl acetate, methyl isobutyl ketone, methyl ethyl ketone, acetone, ethanol, methanol, 2-butanol, 1-butanol, 1-propanol, 2-propanol, 2-methoxyethanol, acetonitrile, tetrahydrofuran, water, and nitromethane. Using two different concentrations for each solvent system, the compound of Formula I was dissolved in the solvent and subjected to heat/cool cycles between room temperature and 50° C. (8 hour cycles) for 24 hours, followed by cooling at 4° C. for 24 hours, and cooling at −20° C. for another 24 hours. None of the single solvent systems afforded a solid form of the compound of Formula I.

Binary solvent systems were also tested for the preparation of a solid form of the compound of Formula I. Using the solvents listed above, other than water and heptane, the compound of Formula I was dissolved, and water, heptane or cyclohexane was added as the antisolvent to reduce the solubility of the compound of Formula I in the solvent mixture. Several binary solvent systems were identified that afforded a solid form: methanol/water, ethanol/water, 2-propanol/water and 2-methoxyethanol/water. Many solvent systems tested failed to provide an amorphous solid form of the compound of Formula I. Surprisingly, while 2-propanol/water afforded an amorphous solid form of the compound of Formula I, 1-propanol/water did not. In addition, 1-butanol/water and 2-butanol/water did not afford an amorphous solid form of the compound of Formula I. The solvent combination can also be subjected to cooling from room temperature to −10° C. at 0.1° C./minute and holding at −10° C., or −20° C. For example, the binary solvent system of tert-butylmethyl ether/heptane provided an amorphous solid form of the compound of Formula I with cooling to −20° C.

Accordingly, the present invention provides an amorphous solid form of a compound of Formula I:

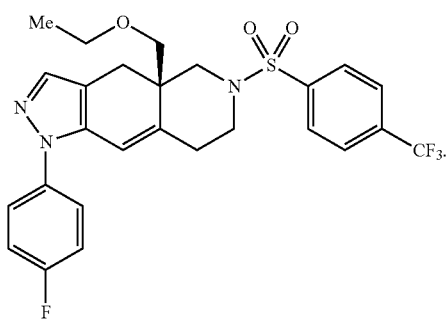

(I)

Figure 2:
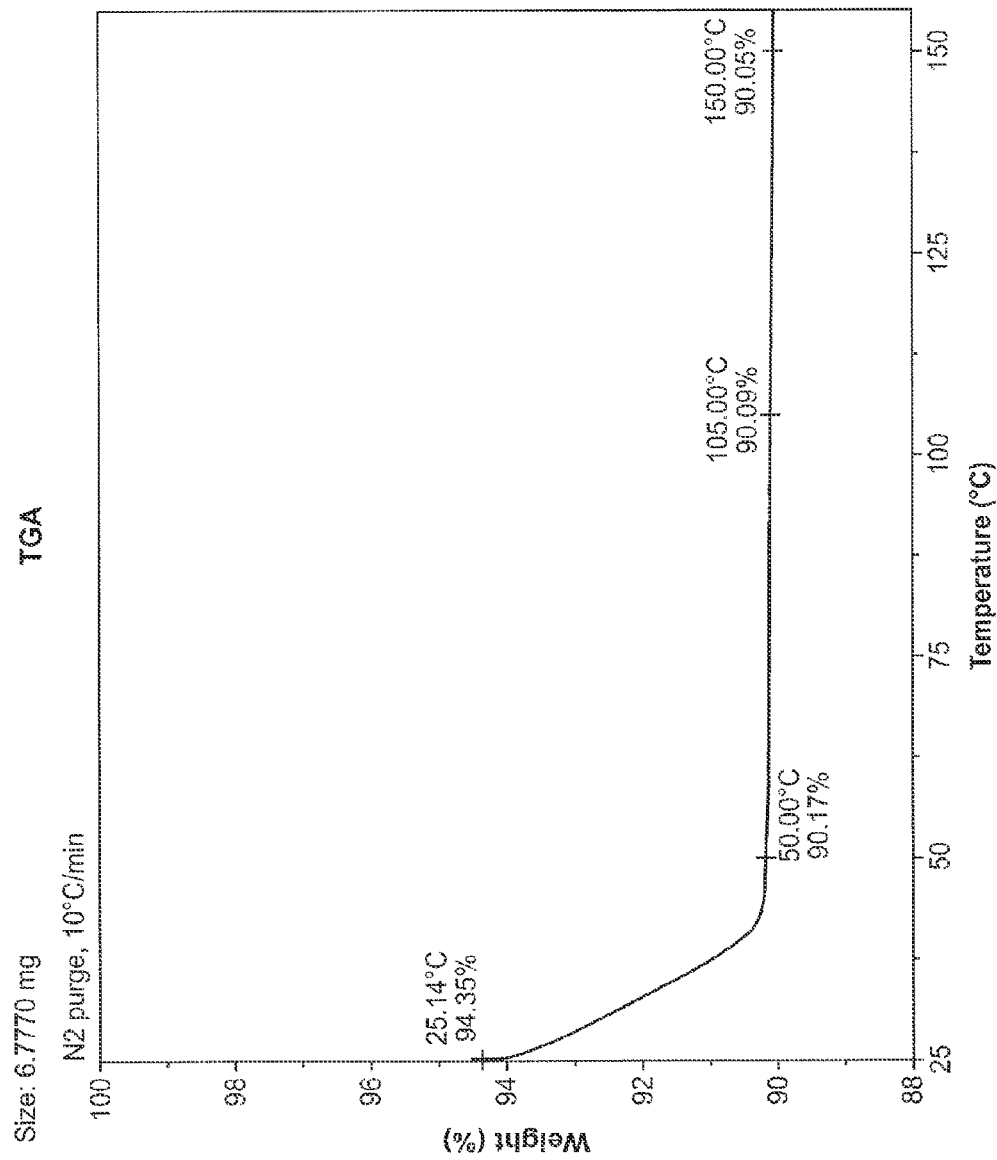
FIG. 2 shows the thermal gravimetric analysis (TGA) of the compound of Formula I.
Figure 3:
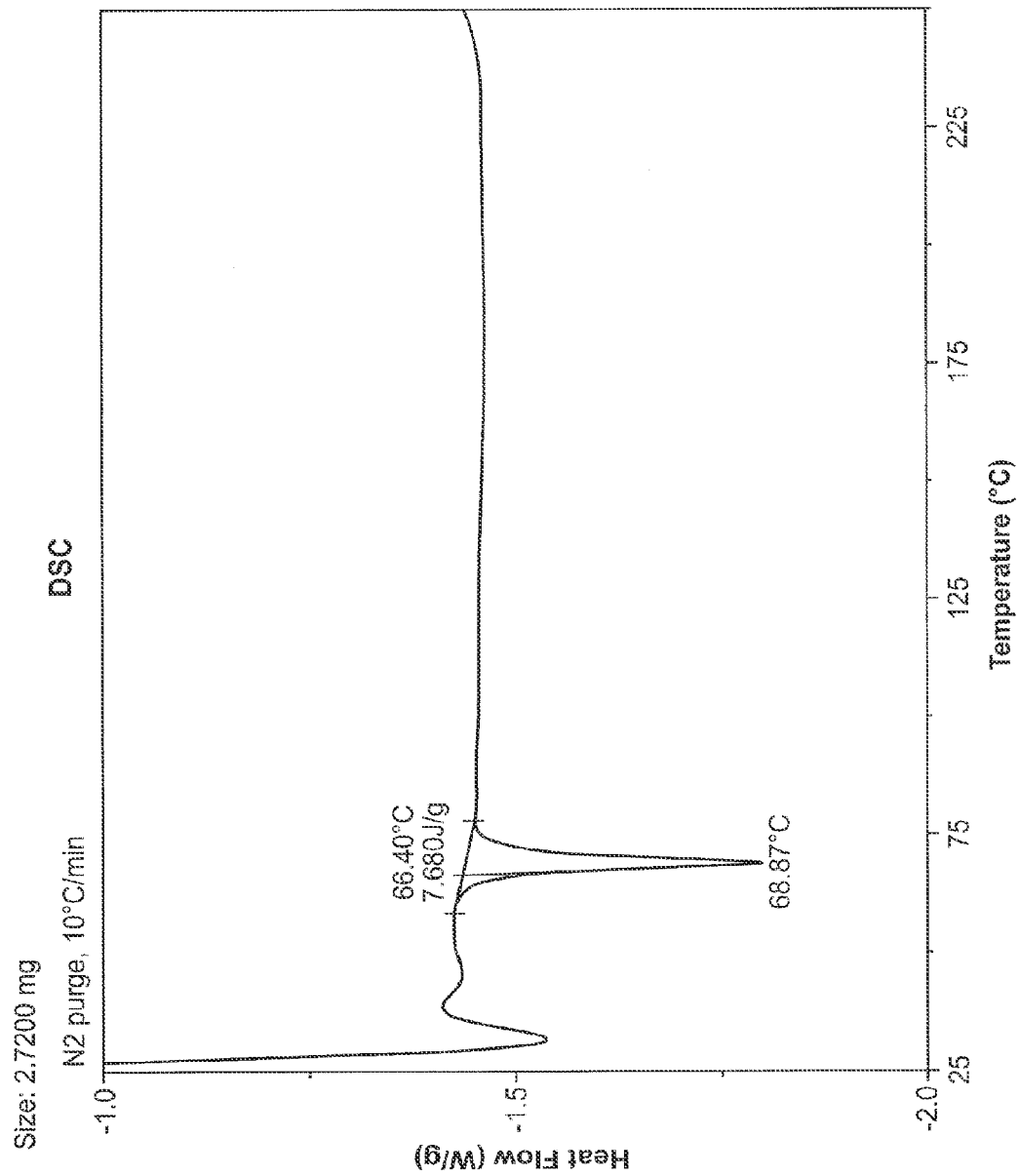
FIG. 3 shows the differential scanning calorimetry (DSC) of the compound of Formula I.

In other embodiments, the compound of Formula I is characterized by an X-ray diffraction pattern, substantially as depicted in FIG. 1. Analysis by thermal gravimetric analysis (TGA) demonstrates a weight loss for the compound of Formula I of about 10% upon heating to 40-45° C., with no additional weight loss up to about 150° C. (see FIG. 2). Analysis by differential scanning calorimetry (DSC) showed an endothermic peak for the amorphous solid form of the compound of Formula I at about 66° C. (see FIG. 3).

Amorphous solid forms of the compound of Formula I can be prepared by a variety of methods. In some embodiments, amorphous solid forms can be prepared by dissolving the compound of Formula I in a good solvent at an elevated temperature to make a saturated solution, and then allowing the solution to cool such that the compound of Formula I comes out of solution to form a precipitate.

Alternatively, amorphous solid forms of the compound of Formula I can be prepared by dissolving the compound of Formula I in a good solvent, and then adding an antisolvent to the good solvent. The antisolvent is a solvent in which the compound of Formula I is not soluble or is poorly soluble, such that the solubility of the compound of Formula I in the mixture of the good solvent and antisolvent is reduced to the point that the compound of Formula I comes out of solution. Solvents useful for dissolving the compound of Formula I include, but are not limited to, dichloromethane, chlorobenzene, toluene, anisole, 1,4-dioxane, tert-butylmethyl ether, butyl acetate, isopropyl acetate, ethyl acetate, methyl isobutyl ketone, methyl ethyl ketone, acetone, ethanol, methanol, 2-butanol, 1-butanol, 1-propanol, 2-propanol, 2-methoxyethanol, acetonitrile, tetrahydrofuran, nitromethane, acetic acid, dimethylformamide, dimethylsulfoxide, and N-methylpyrrolidinone. Other good solvents are useful in the present invention.

Antisolvents useful in the method of the present invention include, but are not limited to, a polar-protic solvent, a $C_5$-$C_{10}$ alkyl and a $C_5$-$C_{10}$ cycloalkyl. Polar protic solvents useful as the antisolvent in the present invention include, but are not limited to, water. A $C_5$-$C_{10}$ alkyl useful as the antisolvent in the present invention include, but are not limited to, pentane, hexane, heptane, octane, nonane, decane, and isomers thereof. The $C_5$-$C_{10}$ alkyl can be linear or branched, saturated or unsaturated. The antisolvent can also be a $C_5$-$C_{10}$ cycloalkyl such as cyclopentane, cyclohexane, cycloheptane, cyclooctane, cyclononane and cyclodecane. The $C_5$-$C_{10}$ cycloalkyl can be partially or fully saturated or unsaturated. Other solvents are useful as the antisolvent of the present invention.

In another embodiment, the present invention provides a method of preparing an amorphous solid form of a compound of Formula I. In one step, the method involves dissolving the compound of Formula I in a solvent of acetone, methanol, ethanol, 2-propanol or 2-methoxyethanol, to prepare a first solution. In another step, the method involves contacting the first solution with water, thereby precipitating the compound of Formula I. In other embodiments, the solvent is methanol, ethanol, 2-propanol or 2-methoxyethanol. In some other embodiments, the solvent is methanol, ethanol or 2-propanol. In still other embodiments, the solvent is ethanol.

The ratio of solvent to antisolvent can be any useful ratio. In some embodiments, the ratio of solvent to antisolvent is from about 5:1 to about 1:10 (vol/vol). In other embodiments, the ratio of solvent to antisolvent is from about 2:1 to about 1:2 (vol/vol). In some other embodiments, the ratio of solvent to antisolvent is about 1:1 (vol/vol). In still other embodiments, the ratio of solvent to antisolvent is from about 1:1 to about 1:5 (vol/vol). In yet other embodiments, the ratio of solvent to antisolvent is about 10:1, 9:1, 8:1, 7:1, 6:1, 5:1, 4:1, 3:1, 2:1, 1:1, 1:2, 1:3, 1:4, 1:5, 1:6, 1:7, 1:8, 1:9 or about 1:10 (vol/vol). Other ratios of solvent to antisolvent are useful in the present invention.

In some embodiments, the antisolvent is added to the first solution. In other embodiments, the first solution is added to the antisolvent. When the first solution is added to the antisolvent, the antisolvent can be stirred vigorously and the first solution added dropwise in order to precipitate the compound of Formula I. For example, when the antisolvent is water, the first solution can be added to the water.

In other embodiments, the present invention provides a method of preparing an amorphous solid form of a compound of Formula I. In one step, the method involves dissolving the compound of Formula I in 1,4-dioxane, to prepare a first solution. In another step, the method involves contacting the first solution with heptane, thereby precipitating the compound of Formula I.

In some other embodiments, the present invention provides a method of preparing an amorphous solid form of a compound of Formula I using a binary solvent system of tert-butylmethyl ether and heptane. In one step, the method involves dissolving the compound of Formula I in tent-butylmethyl ether, to prepare a first solution. In another step, the method involves contacting the first solution with heptane, to prepare a second solution. The method also involves cooling the second solution to less than about 0° C., thereby precipitating the compound of Formula I. In some embodiments, the second solution is cooled to about −20° C. Other temperatures are useful for the preparation of amorphous solid forms of the compound of Formula I. The second solution can be cooled for any suitable period of time. In some embodiments, the cooling can be for several minutes or an hour. In other embodiments, the cooling can be for several hours, or up to a day. In still other embodiments, the cooling can be for several days, such as 1, 2, 3, 4, 5, or more days.

Following precipitation, the solid form of the compound of Formula I is isolated by filtration and dried.

I. EXAMPLES

Example 1

Precipitation of Formula I from Single-Solvent Mixtures

The compound of Formula I was dissolved in the solvent and subject to heat/cool cycles between room temperature and 50° C. (8 hour cycles) for 24 hours, followed by cooling at 4° C. for 24 hours, and cooling at −20° C. for another 24 hours.

TABLE 1

Precipitation from single solvent mixtures

| Solvent | Product I[1] | Product II[2] |
|---|---|---|
| Dichloromethane | Clear Solution | Oil |
| Chlorobenzene | Clear Solution | Oil |
| Toluene | Clear Solution | Oil |
| Anisole | Clear Solution | Oil |
| Heptane | Gum | — |
| 1,4-Dioxane | Clear Solution | Oil |
| Tert-Butylmethyl ether[2] | Clear Solution | Oil |
| Butyl acetate | Clear Solution | Oil |
| Isopropyl acetate | Clear Solution | Oil |
| Ethyl acetate | Clear Solution | Oil |
| Methyl isobutyl ketone | Clear Solution | Oil |
| Methyl ethyl ketone | Clear Solution | Oil |
| Acetone | Clear Solution | Oil |
| Ethanol | Clear Solution | Oil |
| Methanol | Clear Solution | Glass |

TABLE 1-continued

Precipitation from single solvent mixtures

| Solvent | Product I[1] | Product II[2] |
|---|---|---|
| 2-Butanol | Clear Solution | Oil |
| 1-Butanol | Clear Solution | Oil |
| 1-Propanol | Clear Solution | Oil |
| 2-Propanol | Clear Solution | Oil |
| 2-Methoxyethanol | Clear Solution | Oil |
| Acetonitrile | Clear Solution | Oil |
| Tetrahydrofuran | Clear Solution | Oil |
| Water | Gum | — |
| Nitromethane | Clear Solution | Oil |

[1]Concentration is 25-30 mg/0.5 mL.
[2]Concentration is 25-30 mg/0.1 mL. Process also involved sonication at room temperature for 10 minutes and evaporation of the solvent.

Example 2

Precipitation of Formula I from Solvent:Antisolvent Mixtures

Formula I was dissolved in a suitable solvent at room temperature. An anti-solvent was added in the appropriate ratio, and the slurry was stirred at room temperature (unless provided otherwise). Any solid that formed was isolated by filtration and dried.

TABLE 2

Precipitation from alcohol:antisolvent mixtures

| Solvent | Antisolvent | Solvent:Antisolvent Ratio | Product[1] |
|---|---|---|---|
| Methanol | Water | 1:1 | Precipitate |
| Methanol | Water | 10:1 | No precipitate |
| Ethanol | Water | 1:1 | Precipitate |
| Ethanol | Water | 10:1 | No precipitate |
| Ethanol | Cyclohexane[2] | 1:2 | No precipitate |
| 1-Propanol | Water | 1:1 | No precipitate |
| 1-Propanol | Water | 10:1 | No precipitate |
| 1-Propanol | Cyclohexane[2] | 1:2 | No precipitate |
| 2-Propanol | Water | 1:1 | Precipitate |
| 2-Propanol | Water | 10:1 | No precipitate |
| 1-Butanol | Water | 2:1 | No precipitate |
| 2-Butanol | Water | 2:1 | No precipitate |
| 2-Methoxyethanol | Water | 1:1 | Precipitate |
| 2-Methoxyethanol | Water | 10:1 | No precipitate |
| 2-Methoxyethanol | Cyclohexane[2] | 1:2 | No precipitate |

[1]Any precipitate formed is an amorphous precipitate.
[2]Cooling from room temperature to −10° C. at 0.1° C./minute and holding at −10° C. for four days.

TABLE 3

Precipitation from solvent:antisolvent mixtures

| Solvent | Antisolvent | Solvent:Antisolvent Ratio | Product[1] |
|---|---|---|---|
| Dichloromethane | Heptane | 1:2 | No precipitate |
| Chlorobenzene | Heptane | 1:2 | No precipitate |
| Toluene | Heptane | 1:2 | No precipitate |
| Anisole | Heptane | 1:2 | No precipitate |
| 1,4-Dioxane | Heptane | 1:2 | Precipitate |
| Tert-Butylmethyl ether[2] | Heptane | 1:2 | No precipitate |
| Butyl acetate | Heptane | 1:2 | No precipitate |
| Isopropyl acetate | Heptane | 1:2 | No precipitate |
| Ethyl acetate | Heptane | 1:2 | No precipitate |
| Methyl isobutyl ketone | Heptane | 1:2 | No precipitate |

TABLE 3-continued

Precipitation from solvent:antisolvent mixtures

| Solvent | Antisolvent | Solvent:Antisolvent Ratio | Product[1] |
| --- | --- | --- | --- |
| Methyl ethyl ketone | Heptane | 1:2 | No precipitate |
| Acetone | Water | 1:1 | Precipitate |
| Acetone | Water | 10:1 | No precipitate |
| Acetonitrile | Water | 1:2 | No precipitate |
| Acetonitrile | Water | 10:1 | No precipitate |
| Tetrahydrofuran | Heptane | 1:2 | No precipitate |
| Nitromethane | Heptane | 1:2 | No precipitate |
| Acetic acid | Water | 1:3 | No precipitate |
| Dimethylformamide | Water | 1:3 | No precipitate |
| Dimethylsulfoxide | Water | 1:3 | No precipitate |
| N-methylpyrrolidinone | Water | 1:3 | No precipitate |

[1]Any precipitate formed is an amorphous precipitate.
[2]After cooling to −20° C. for 5 days, an amorphous precipitate was formed.

Example 3

Precipitation of Formula I from Ethanol/Water

The precipitation was run under nitrogen. A 22-L baffled, jacketed reaction flask equipped with overhead stirrer, thermocouple, addition funnel, and Julabo HTU was rinsed with a mixture of 1 L of water and 0.25 L ethanol before use. Water was charged to the flask and stirred, with the Julabo setpoint at 20.0° C. Purified compound of Formula I from the rotovap bulb (381.1 g) was dissolved in ethanol (4.0 L), and the solution filtered thru a rinsed plug of glass wool into a rinsed Pyrex bottle. The rotovap bulb and funnel were rinsed with ethanol (0.3 L). The solution was mixed, and then transferred (in 500 mL portions) to the addition funnel. The solution was added in a thin stream over 1 h 48 min to the vigorously stirred water, generating a white precipitate. The temperature was held between 21 and 25° C. during addition of the compound of Formula I. The empty Pyrex bottle was rinsed with ethanol (50 mL), and the rinse added to the addition funnel and then to the flask. The white suspension was stirred at 20-25° C. for 78 min. Solid was isolated by vacuum filtration on a medium fritted-glass funnel; the cake cracked and shrank. The flask was rinsed with 4:1 water/ethanol (1900 mL) and the rinses added to the funnel. The cake was deliquored, then transferred to Pyrex drying trays, and the lumps broken up. The trays were placed in vacuum drying ovens held at 40-50° C., under a nitrogen sweep until at constant weight. 364 g of the compound of Formula I were isolated.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:
1. An amorphous solid form of a compound of Formula I:

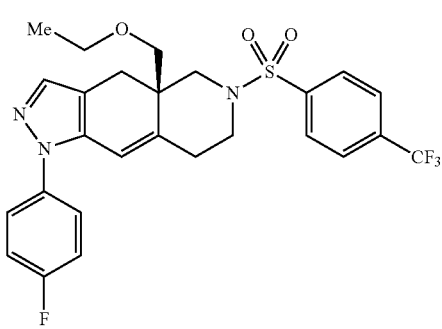

(I)

prepared by the method comprising:
dissolving the compound of Formula I in a solvent selected from the group consisting of acetone, methanol, ethanol, 2-propanol and 2-methoxyetha.nol, to prepare a first solution; and
contacting the first solution with water, thereby preparing the amorphous solid form of the compound of Formula I.

2. The compound of claim 1, wherein the solvent is selected from the group consisting of methanol, ethanol, 2-propanol and 2-methoxyethanol.

3. The compound of claim 2, wherein the solvent is selected from the group consisting of methanol, ethanol, and 2-propanol.

4. The compound d of claim 3, wherein the solvent is ethanol.

5. The compound of claim 4, wherein the first solution is added to the water.

6. The compound of claim 1, wherein the ratio of solvent to water is from about 5:1 to about 1:10 (vol/vol).

7. The compound of claim 6, wherein the ratio of solvent to water is from about 2:1 to about 1:2 (vol/vol).

8. The compound of claim 6, wherein the ratio of solvent water is about 1:1 (vol/vol).

9. The compound of claim 1, wherein the ratio of solvent to water is from about 1:1 to about 1:5 (vol/vol).

10. The compound of claim 1, characterized by an X-ray diffraction pattern, substantially as depicted in FIG. 1.

11. An amorphous solid form of a compound of Formula I:

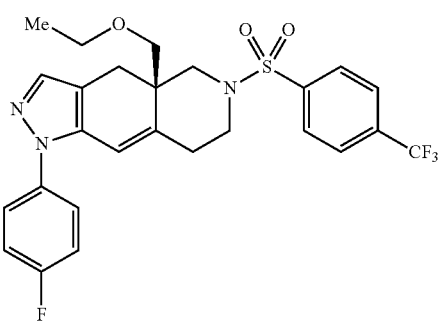

(I)

, prepared by the method comprising:
dissolving the compound of Formula I in 1,4-dioxane, to prepare a first solution; and
contacting the first solution with heptane, thereby preparing the amorphous solid form of the compound of Formula I.

12. The compound of claim 11, characterized by an X-ray diffraction pattern, substantially as depicted in FIG. 1.

13. An amorphous solid form of a compound of Formula I:

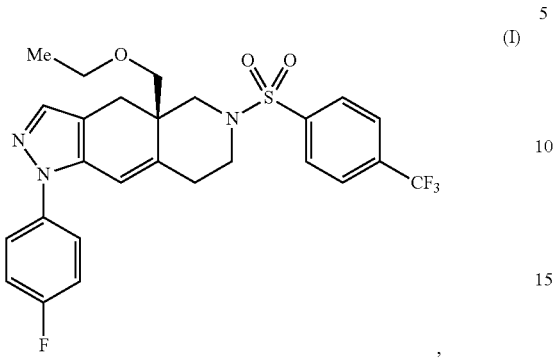

(I)

, prepared by the method comprising:
dissolving the compound of Formula I in tert-butylmethyl ether, to prepare a first solution; and
contacting the first solution with heptane, to prepare a second solution; and
cooling the second solution to less than about 0° C., thereby preparing the amorphous solid form of the compound of Formula I.

14. The compound of claim 13, characterized by an X-ray diffraction pattern, substantially as depicted in FIG. 1.

* * * * *

UNITED STATES PATENT AND TRADEMARK OFFICE
CERTIFICATE OF CORRECTION

Page 1 of 1

PATENT NO. : 8,889,867 B2
APPLICATION NO. : 13/889130
DATED : November 18, 2014
INVENTOR(S) : Robin Clark et al.

It is certified that error appears in the above-identified patent and that said Letters Patent is hereby corrected as shown below:

In the Specification,

"CROSS-REFERENCE TO RELATED APPLICATIONS" section:

Column 1 line 8 please delete "U.S. Provisional Application No. 61/177,483, filed May 13, 2009," and insert --U.S. Provisional Application No. 61/177,483, filed May 12, 2009,--

Signed and Sealed this
Seventeenth Day of March, 2015

Michelle K. Lee
*Director of the United States Patent and Trademark Office*